United States Patent [19]

France et al.

[11] Patent Number: 5,169,640

[45] Date of Patent: Dec. 8, 1992

[54] PHARMACEUTICAL COMPOSITIONS

[75] Inventors: Gordon France, Digswell; Graham S. Leonard, St. Albans; Kevin E. Pearmain, Hitchin, all of England

[73] Assignee: Smith Kline & French Laboratories, Ltd., Welwyn Garden City

[21] Appl. No.: 297,197

[22] PCT Filed: May 4, 1988

[86] PCT No.: PCT/GB88/00350

§ 371 Date: Jan. 4, 1989

§ 102(e) Date: Jan. 4, 1989

[87] PCT Pub. No.: WO88/08704

PCT Pub. Date: Nov. 17, 1988

[30] Foreign Application Priority Data

May 8, 1987 [GB] United Kingdom ............... 8710965

[51] Int. Cl.$^5$ ............................................. A61K 9/26
[52] U.S. Cl. .................................. 424/470; 424/459; 424/489
[58] Field of Search ............... 424/470, 464, 441, 465

[56] References Cited

U.S. PATENT DOCUMENTS

| | | | |
|---|---|---|---|
| 4,676,984 | 6/1987 | Wu et al. | 424/689 |
| 4,681,756 | 7/1987 | Mergens et al. | 425/451 |
| 4,748,023 | 5/1988 | Tamas | 424/465 |

FOREIGN PATENT DOCUMENTS

| | | |
|---|---|---|
| A0003589 | 8/1979 | European Pat. Off. |
| A0138540 | 4/1985 | European Pat. Off. |
| M6885 | 4/1969 | France |

OTHER PUBLICATIONS

Steinberg et al., New England J. of Med., vol. 307, No. 7, pp. 400-404.
Chemical Abstracts, vol. 102, 1985, p. 375, abstract No. 137799m Columbus, Ohio, US.

Primary Examiner—Thurman K. Page
Assistant Examiner—Leon R. Horne
Attorney, Agent, or Firm—Dara L. Dinner; Stephen Venetianer; Edward T. Lentz

[57] ABSTRACT

The invention provides a solid pharmaceutical dosage form comprising:
(i) cimetidine; and
(ii) antacid, wherein at least part of the antacid is in the form of granules comprising a freely water-soluble solid diluent, the antacid, and a rapidly swellable water-insoluble disintegrant.

Compositions of this type overcome the problem of the reduced bioavailability of cimetidine which can occur when cimetidine is co-administered with antacids.

17 Claims, No Drawings

PHARMACEUTICAL COMPOSITIONS

This invention relates to a solid pharmaceutical dosage form comprising cimetidine and an antacid and to a method for the preparation of such a dosage form.

Cimetidine is a histamine $H_2$-antagonist which has been described in U.K. Patent Specification 1,397,436. Cimetidine has been shown to be useful in the treatment of duodenal, gastric, recurrent and stomal ulceration, and reflux oesophagitis and in the management of patients who are at high risk from haemorrhage of the upper gastrointestinal tract.

Cimetidine and antacids are frequently co-administered (see for example the article by H. Allgayer and G. Paumgartner, *Arzneim Forsch.* pp. 870–871, 34, No. 8 (1984)). The rationale for co-administration is that antacid brings about rapid relief from the symptoms of excess stomach acidity by neutralising the acid whereas the cimetidine brings about more sustained relief by inhibiting secretion of more acid.

However, it is well known (see Allgayer and Paumgartner, and Steinberg et al, *New England J. Medicine*, 1982; 307, 400–4) that when cimetidine is co-administered with antacids, particularly aluminium hydroxide and magnesium hydroxide, there is frequently a substantial reduction in the bioavailability of the cimetidine. The reason for the reduction in bioavailability is not clear, although a number of attempts to discover the mechanism responsible for the problem have been reported in the literature. Thus for example Allgayer and Paumgartner were unable to demonstrate why the decrease in bioavailability occurs although they indicated that it was not due to binding of the cimetidine by the antacid.

The benefits, particularly in terms of patient compliance with a treatment regimen, which would arise from an effective combination product containing cimetidine and an antacid, would be expected to be considerable. However, the problem of loss of bioavailability, and the lack of understanding of its cause have, up until now, precluded the development of such a product, as far as we are aware.

It has now been found, surprisingly, that the problem of the loss of bioavailability of the cimetidine can be solved by granulating at least part of the antacid separately, and in a particular manner, prior to mixing with the cimetidine.

In a first aspect, therefore, the invention provides a solid pharmaceutical dosage form comprising:
(i) cimetidine; and
(ii) antacid, wherein at least part of the antacid is in the form of granules comprising a freely water-soluble solid diluent, the antacid, and a rapidly swellable water-insoluble disintegrant.

It is preferred that at least 50% by weight of the total antacid in the dosage form is granulated in the particular manner described above in (ii). In general, as the ratio of antacid to cimetidine is increased, it is desirable to increase the proportion of antacid granulated in this way. In one preferred embodiment of the invention, substantially all of the antacid is thus granulated.

The term "freely soluble" is known in the art as referring to a particular level of solubility; thus, in the U.S. Pharmacopoeia, it is defined as meaning that a substance can form a 10% solution in a solvent. Preferably the substance can form at least a 50% solution in water.

Typically the freely water-soluble solid diluent is a sugar and/or sugar alcohol.

Examples of sugars and sugar alcohols are sucrose, lactose, sorbitol, xylitol and mannitol, preferred diluents being lactose, sorbitol and sorbitol/lactose mixtures.

It is preferred that the ratio (w/w) of solid diluent to antacid is in the range 1:1 to 8:1, particularly approximately 3:1.

Typically the rapidly swellable water-insoluble disintegrants are synthetic or semi-synthetic polymers of a type known in the art as superdisintegrants (see for example International Patent Application No. PCT/US 87/00302, published as WO 87/05804, and references cited therein). Examples of superdisintegrants include cross-linked polymeric disintegrants such as cross-linked carboxymethyl celluloses, particularly croscarmellose sodium and croscarmellose calcium, cross-linked polyvinyl pyrrolidone, and sodium starch glycolate.

Typically the disintegrant is present in an amount from approximately 0.5% (w/w) to approximately 8% (w/w), relative to the total weight of the granules, particularly approximately 2% (w/w).

The antacid-containing granules are preferably formed by a dry granulation process, for example by compacting using a roller compacter or a tablet press, followed by milling the compact to give granules that have low friability. Suitably, in such a case, the mixture for granulating can contain a lubricant. Examples of lubricants are stearates such as magnesium stearate, and stearic acid.

The antacid typically is selected from aluminium hydroxide, magnesium hydroxide, magnesium carbonate, calcium carbonate and co-dried gels, for example aluminium hydroxide-magnesium carbonate co-dried gel. A particular antacid is aluminium hydroxide or a mixture of aluminium hydroxide and magnesium hydroxide.

In general a dosage form contains between 5 mEq and 30 mEq of antacid, and preferably approximately 14 mEq.

The cimetidine will usually be present in an amount from 50 mg to 800 mg per dosage form, and typically a dosage form will contain 100 mg or 200 mg of cimetidine.

Examples of dosage forms include tablets, capsules and lozenges.

The compositions of the present invention can be in the form of chewable tablets, that is to say tablets which disintegrate readily in the mouth when chewed. With chewable tablets, the pronounced bitter taste of cimetidine means that in practice it is necessary to provide a means of masking the bitter taste. One means of masking the bitter taste is to coat the cimetidine with a coating agent in an amount effective to mask the bitter taste but which does not significantly affect the bioavailability of the cimetidine.

One such coating agent is dimethylaminoethylmethacrylate/methacrylic acid ester co-polymer which is sold under the trade name Eudragit E. According to a copending patent application (reference no. 11940) claiming priority from British patent application Nos. 8710965 and 8710966, cimetidine can be granulated using Eudragit E, in an amount 2–20% (w/w) relative to the cimetidine, as the granulating agent. By employing a Eudragit E loading in this range, the bitter taste of cimetidine is masked but the dissolution characteristics and hence bioavailability remain acceptable.

In addition to cimetidine and antacid-containing granules, the solid dosage forms of the present invention can contain other pharmaceutical excipients. Thus, for example, where the dosage form is subject to a compression step, the dosage form can additionally contain a lubricating agent, typically stearic acid or a stearate salt and particularly magnesium stearate.

The compositions of the present invention can also contain additional sweeteners, for example aspartame, cyclamate and saccharin, and colouring and flavouring agents as known in the art.

The invention will now be illustrated in greater detail by the following Examples.

EXAMPLE 1

100 mg Chewable Tablet

Ingredient

| | mg/tablet | % w/w |
|---|---|---|
| Cimetidine Premix Granules | | |
| Cimetidine | 100.0 | 90.9 |
| Eudragit E100* | 10.0 | 9.1 |
| Antacid (Al/Mg) Granules | | |
| Direct Compression Sorbitol | 590.0 | 34.01 |
| Direct Compression Lactose | | |
| Crystalline | 325.0 | 18.73 |
| Spray dried | 325.0 | 18.73 |
| Croscarmellose Sodium Type A | 30.0 | 1.73 |
| Dried Aluminium Hydroxide Gel** | 250.0 | 14.41 |
| Magnesium Hydroxide** | 200.0 | 11.53 |
| Magnesium Stearate | 15.0 | 0.86 |
| | 1735.0 | 100.00 |
| Tableting Mix for Compression | | |
| Cimetidine Premix Granules | 110.0 | |
| Antacid (Al/Mg) Granules | 1735.0 | |
| Aspartame | 3.0 | |
| Peppermint | 15.0 | |
| Tutti Frutti | 5.0 | |
| Spearmint | 5.0 | |
| Lactose | 200.0 | |
| Croscarmellose Sodium Type A | 30.0 | |
| Magnesium Stearate | 15.0 | |
| | 2118.0 | |

*Added to the cimetidine by granulation as a 40% w/v solution in methylene chloride. Solvent lost in processing.
**Quantities used adjusted for the potencies of raw materials: Standard quantity of Dried Aluminium Hydroxide gel is equivalent to 117.5 mg/tablet $Al_2O_3$ or 180 mg/tablet Aluminium Hydroxide $(Al(OH)_3)$.

Process Description

A 40% w/v solution of the Eudragit E100 in methylene chloride is added with mixing to the cimetidine and blended until granules are formed. The resulting granules are dried and then sieved through a 16 mesh screen.

The aluminium hydroxide, magnesium hydroxide and other ingredients for the antacid granules are sieved through a 12 mesh (1.4 mm) screen and mixed together. The resulting mix is compressed on a rotary tablet press and the resulting compacts are milled using a 12 mesh screen.

The cimetidine granules, antacid granules and extra-granular excipients are put into a cone blender and mixed thoroughly. The resulting mix is discharged from the blender and compressed on a suitable rotary tablet press fitted with the appropriate punches.

EXAMPLE 2

200 mg Chewable Tablet

Ingredient

| | mg/tablet | % w/w | |
|---|---|---|---|
| Cimetidine Premix Granules | | | |
| Cimetidine | 200.0 | 90.9 | |
| Eudragit E100* | 20.0 | 9.1 | |
| Antacid (Al/Mg) Granules | | | |
| Sorbitol: Direct Compression Grade | 295.0 | 34.01 | |
| Lactose: Direct Compression Grade | | | |
| Spray dried | 162.5 | 18.73 | |
| Crystalline | 162.5 | 18.73 | |
| Dried Aluminium Hydroxide Gel | 125.0 | 14.41 | |
| Magnesium Hydroxide | 100.0 | 11.53 | |
| Croscarmellose Sodium Type A | 15.0 | 1.73 | |
| Magnesium Stearate | 7.5 | 0.86 | |
| | 867.5 | 100.00 | |
| Tableting Mix for Compression | | | |
| Cimetidine Premix Granules | 220.0 | | |
| Antacid (Al/Mg) Granules | 867.5 | | |
| Dried Aluminium Hydroxide Gel | 125.0 | | |
| Magnesium Hydroxide | 100.0 | | |
| Sorbitol: Direct Compression Grade | 295.0 | | |
| Lactose: Direct Compression Grade | | | |
| Spray dried | 162.5 | | |
| Crystalline | 162.5 | | |
| Croscarmellose Sodium Type A | 45.0 | | |
| Aspartame | 3.0 | | |
| Aniseed | 20.0 | | |
| Butterscotch | 20.0 | | |
| Magnesium Stearate | 22.5 | or | 37.5 |
| TOTAL | 2048.0 | | 2063.0 |

*Added to the cimetidine by granulation as a 40% w/v solution in methylene chloride. Solvent lost in processing.

Process Description

The cimetidine premix granules and antacid granules were prepared according to the method described in Example 1. The cimetidine granules and antacid granules were then blended with the remaining ingredients and compressed on a rotary press fitted with the appropriate tablet punches and dies. The formulations of the following Examples 3 and 4 were prepared in a similar manner.

EXAMPLE 3

200 mg Chewable Tablet

Ingredient

| | mg/tablet | % w/w |
|---|---|---|
| Cimetidine Premix Granules | | |
| Cimetidine | 200.0 | 90.9 |
| Eudragit E100* | 20.0 | 9.1 |
| Antacid (Al/Mg) Granules | | |
| Sorbitol: Direct Compression Grade | 590.0 | 34.01 |
| Lactose: Direct Compression Grade | | |
| Spray dried | 325.0 | 18.73 |
| Crystalline | 325.0 | 18.73 |
| Dried Aluminium Hydroxide Gel | 250.0 | 14.41 |
| Magnesium Hydroxide | 200.0 | 11.53 |
| Croscarmellose Sodium Type A+ | 30.0 | 1.73 |
| Magnesium Stearate | 15.0 | 0.86 |
| | 1735.0 | 100.00 |
| Tableting Mix for Compression | | |
| Cimetidine Premix Granules | 220.0 | |
| Antacid (Al/Mg) | 1735.0 | |

-continued

| | mg/tablet | % w/w |
|---|---|---|
| Granules | | |
| Microcrystalline Cellulose (Avicel PH102)+ | 200.0 | |
| Aspartame | 10.0 | |
| Aniseed | 20.0 | |
| Butterscotch | 20.0 | |
| Magnesium Stearate | 15.0 | |
| TOTAL | 2220.0 | |

*Added to the cimetidine by granulation as a 40% w/v solution in methylene chloride. Solvent lost in processing.
+Croscarmellose Sodium Type A and Avicel PH102 can both be obtained from the FMC Corporation, Philadelphia PA.

EXAMPLE 4

100 mg Chewable Tablet

Ingredient

| | mg/tablet | % w/w |
|---|---|---|
| Cimetidine Premix Granules | | |
| Cimetidine | 100.0 | 90.9 |
| Eudragit E100* | 10.0 | 9.1 |
| Antacid (Al/Mg) Granules | | |
| Lactose: Direct Compression Grade | | |
| Spray dried | 190.0 | 29.23 |
| Crystalline | 190.0 | 29.23 |
| Dried Aluminium Hydroxide Gel | 125.0 | 19.3 |
| Magnesium Hydroxide | 100.0 | 15.38 |
| Croscarmellose Sodium Type A | 30.0 | 4.62 |
| Magnesium Stearate | 15.0 | 2.31 |
| | 650.0 | 100.00 |
| Tableting Mix for Compression | | |
| Cimetidine Premix Granules | 110.0 | |
| Antacid (Al/Mg) Granules | 650.0 | |
| Dried Aluminium Hydroxide Gel | 125.0 | |
| Magnesium Hydroxide | 100.0 | |
| Sorbitol: Direct Compression Grade | 590.0 | |
| Lactose: Direct Compression Grade | | |
| Spray dried | 190.0 | |
| Crystalline | 190.0 | |
| Croscarmellose Sodium Type A | 30.0 | |
| Aspartame | 3.0 | |
| Aniseed | 20.0 | |
| Butterscotch | 20.0 | |
| Magnesium Stearate | 15.0 | |
| Sodium Saccharin | 5.0 | |
| TOTAL | 2048.0 | |

*Added to the cimetidine by granulation as a 40% w/v solution in methylene chloride. Solvent lost in processing.

We claim:

1. A solid pharmaceutical dosage form comprising:
   (i) from about 50 mg. to about 800 mg. of cimetidine; and
   (ii) from about 5 mEq. to about 30 mEq. of an antacid, wherein at least 50% of the total antacid present is in the form of granules which granules further comprise a freely water-soluble solid diluent, the antacid and a rapidly swellable water insoluble disintegrant and wherein said antacid is separately granulated from the cimetidine.

2. A solid pharmaceutical dosage form according to claim 1 wherein substantially all of the antacid present is contained within the granules.

3. A dosage form according to claim 1 wherein the granules are dry-granulated.

4. A dosage form according to claim 1 wherein the highly water-soluble solid diluent is a sugar or a sugar alcohol.

5. A dosage form according to claim 4 wherein the ratio (w/w) of solid diluent to antacid is in the range from approximately 1:1 to approximately 8:1.

6. A dosage form according to claim 1 wherein the disintegrant is a cross-linked carboxymethylcellulose.

7. A dosage form according to claim 1 wherein the antacid is present in an amount from between 5 mEq and 30 mEq.

8. A pharmaceutical tablet composition comprising:
   (i) granules comprising from about 50 mg. to about 800 mg. of cimetidine and a granulating agent wherein the granulating agent is a co-polymer of dimethylaminoethylmethacrylate and methacrylic acid ester in an amount of approximately 10% (w/w) relative to the cimetidine; and
   (ii) from about 5 mEq. to about 30 mEq. of antacid-containing granules comprising aluminium hydroxide and magnesium hydroxide; a solid diluent which is lactose or a mixture of sorbitol and lactose, the ratio (w/w) of diluent to aluminium hydroxide/magnesium hydroxide being approximately 3:1; and a disintegrant which is croscarmellose sodium, the disintegrant being present in an amount of approximately 2% (w/w) relative to the total weight of the antacid-containing granules; wherein the antacid-containing granules are separately formed by dry granulation.

9. A dosage form according to claim 4 wherein the highly water soluble solid diluent comprises a lactose/sorbitol mixture.

10. A dosage form according to claim 5 wherein the ratio is approximately 3:1.

11. A dosage form according to claim 6 wherein the cross-linked carboxymethylcellulose is croscarmellose sodium.

12. A dosage form according to claim 7 wherein the antacid is present in an amount of approximately 14 mEq.

13. A dosage form according to claim 1 wherein the antacid is a mixture of aluminum hydroxide and magnesium hydroxide.

14. A dosage form according to claim 1 which is a chewable tablet.

15. A dosage form according to claim 3 wherein the cimetidine is coated with a coating agent in an amount effective to mask the bitter taste of cimetidine but readily soluble in the stomach to release the cimetidine.

16. A dosage form according to claim 15 wherein the coating agent is a co-polymer of dimethylaminoethylmethacrylate and methacrylic acid esters.

17. A dosage form according to claim 16 wherein the cimetidine is in the form of a granulate and wherein the coating agent, which is present in an amount of 2-20% (w/w) relative to the cimetidine, serves as a granulating agent.

* * * * *